United States Patent
Dannhardt et al.

(10) Patent No.: US 7,078,535 B2
(45) Date of Patent: Jul. 18, 2006

(54) METHOD FOR THE PRODUCTION OF 6-(4-CHLOROPHENYL)-2,2-DIMETHYL-7-PHENYL-2,3-DIHYDRO-1H-PYRROLIZIN-5-YLACETIC ACID

(75) Inventors: Gerd Dannhardt, Mainz (DE); Thomas Kammermeier, Ulm (DE); Philipp Merckle, Blaubeuren-Weiler (DE); Hans-Günter Striegel, Blaustein (DE); Stefan Laufer, Blaubeuren (DE)

(73) Assignee: Merckle GmbH, Blaubeuren (DE)

( * ) Notice: Subject to any disclaimer, the term of this patent is extended or adjusted under 35 U.S.C. 154(b) by 10 days.

(21) Appl. No.: 10/486,911

(22) PCT Filed: Aug. 21, 2002

(86) PCT No.: PCT/EP02/09356

§ 371 (c)(1),
(2), (4) Date: Jun. 4, 2004

(87) PCT Pub. No.: WO03/018583

PCT Pub. Date: Mar. 6, 2003

(65) Prior Publication Data

US 2004/0236117 A1    Nov. 25, 2004

(30) Foreign Application Priority Data

Aug. 23, 2001 (DE) ............................. 101 41 285

(51) Int. Cl.
*C07D 209/52* (2006.01)
*C07D 207/26* (2006.01)

(52) U.S. Cl. ................ 548/516; 548/571; 548/577

(58) Field of Classification Search ............ 548/516, 548/571, 577
See application file for complete search history.

(56) References Cited

U.S. PATENT DOCUMENTS 6,417,371 B1    7/2002  Kammermeier et al.

FOREIGN PATENT DOCUMENTS

| EP | 0 172 371 | 2/1986 |
| EP | 0 397 175 | 11/1990 |
| WO | 95/32970 | 12/1995 |
| WO | 95/32971 | 12/1995 |
| WO | 95/32972 | 12/1995 |

OTHER PUBLICATIONS

Stefan Laufer, et al., "Synthesis and Evaluation of a Novel Series of Pyrrolizine Derivatives as Dual Cyclooxygenase-1 and 5-Lipoxygenase Inhibitors", Archiv Der Pharmazie, vol. 330, pp. 307-312.
Otto Bayer:"Methoden der Organischen Chemie (Houben-Weyl) band VII/2c, Ketone, Teil III", 1977 (With English Translation).
Database Crossfire Beilstein, vol. 19, No. 6, pp. 622-630 1983.
Kraus, et al., "Selective Reduction via Enolate Protection", J. Org. Chem., vol. 45, pp. 4262-4263, 1980.
H. Ahlbrecht, et al., Synthesis, vol. 4, pp. 421-423 1985(With English Translaton:.
Drugs of the Future, 20(10): 1007-1009 1995.
Gerd Dannhardt, et al., Arch. Pharm., vol. 312, pp. 896-907 1979.
Gerd Dannhardt, et al., Arch.. Pharm. vol. 321, pp. 159-162 1988.
Stefan A. Laufer, et al., J. Med. Chem., vol. 37, pp. 1894-1897 1994.
Stefan Laufer, et al., Arch. Pharm. Pharm. Med. Chem. vol. 330, pp. 307-312 1997.
Hubertus Ahlbrecht, et al., SYNTHESIS, pp. 413-416, 1980 (With Partial English Translation).
Database Crossfire Beilstein, vol. 19, No. 6, 1983, pp. 622-630 (with English translation).

*Primary Examiner*—Cecilia J. Tsang
*Assistant Examiner*—Raymond Covington
(74) *Attorney, Agent, or Firm*—Oblon, Spivak, McClelland, Maier & Neustadt, P.C.

(57) ABSTRACT

The invention relates to a process for the preparation of 6-(4-chlorophenyl)-2,2-dimethyl-7-phenyl-2,3-dihydro-1H-pyrrolizin-5-ylacetic acid, in which 5-benzyl-3,3-dimethyl-3,4-dihydro-2H-pyrrole is reacted with ω-bromo-4-chloro-acetophenone with formation of 6-(4-chlorophenyl)-2,2-dimethyl-7-phenyl-2,3-dihydro-1H-pyrrolizine and the acetic acid group is introduced into the 5-position, 5-benzyl-3,3-dimethyl-3,4-dihydro-2H-pyrrole being obtained by hydrogenation of 2,2-dimethyl-4-oxo-5-phenylvaleronitrile or a ketal thereof. The invention also relates to processes for the preparation of intermediates occurring in the above process.

48 Claims, No Drawings

METHOD FOR THE PRODUCTION OF 6-(4-CHLOROPHENYL)-2,2-DIMETHYL-7-PHENYL-2,3-DIHYDRO-1H-PYRROLIZIN-5-YLACETIC ACID

The present invention relates to a process for the preparation of 6-(4-chlorophenyl)-2,2-dimethyl-7-phenyl-2,3-dihydro-1H-pyrrolizin-5-ylacetic acid (ML3000) and for the preparation of intermediates occurring in this process.

ML 3000 is a promising inhibitor of cyclooxygenase and 5-lipoxygenase and is thus suitable for the treatment of diseases of the rheumatic type and for the preventive treatment of allergically induced diseases, for this see, for example, Drugs of the Future 1995, 20 (10): 1007–1009. In this publication, a possible route for preparation is also found. Further preparation possibilities are described in EP-A-397175, WO95/32970, WO95/32971, WO95/32972, Archiv der Pharmazie 312, 896–907 (1979); and 321, 159–162 (1988), J. Med. Chem. 1994 (37), 1894–1897, Arch. Pharm. Med. Chem. 330, 307–312 (1997). In all these syntheses, the pyrrolizine parent structure is synthesized according to the method shown in the reaction scheme:

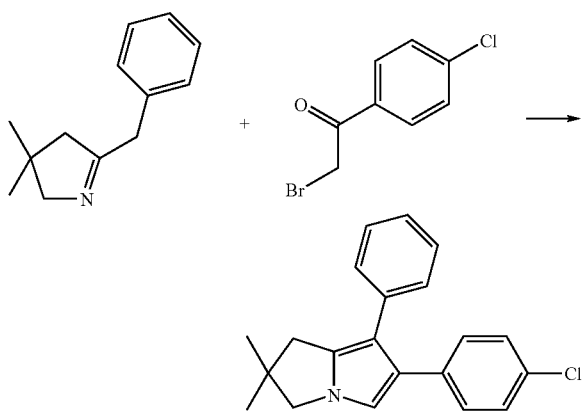

The reaction is carried out in methylene chloride, ethanol or diethyl ether. The hydrogen bromide formed in the reaction is trapped by addition of aqueous sodium bicarbonate solution.

The introduction of the acetic acid radical into position 5 can be carried out by reaction with diazoacetic ester, an oxalic ester chloride or oxalyl chloride und subsequent hydrolysis or hydrolysis and reduction of the keto group using hydrazine.

Arch. Pharm. 312, 896–907 (1979) describes the following reaction:

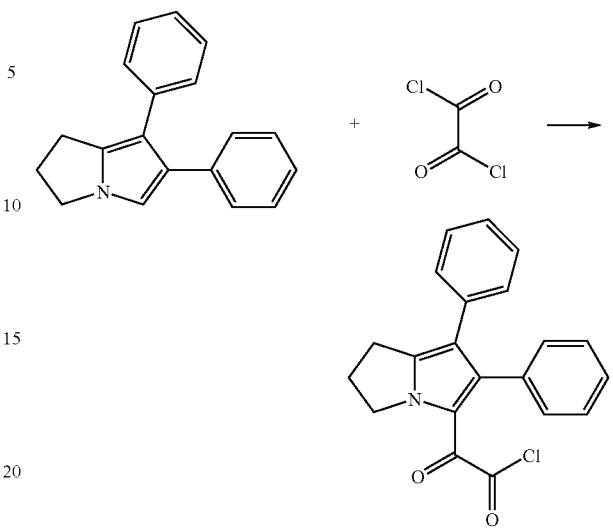

The reaction is carried out in benzene as solvent. The COCOCl grouping, however, is not then converted into the acetic acid group, but reacted with diethylamine.

Crude ML 3000, which is obtained according to the hydrazine process as a potassium salt and which is then precipitated from the reaction mixture rendered acetic with mineral acid, contains, in addition to the potassium salts which are poorly soluble in water, also hydrazine, by-products and decomposition products (decarboxylation product and dimer) as an impurity. This requires additional purification operations.

The patent application PCT/EP 01/00852 discloses a process for the preparation of ML 3000 by reaction of 6-(4-chlorophenyl)-2,2-dimethyl-7-phenyl-2,3-dihydro-1H-pyrrolizine with oxalyl chloride and hydrazine, followed by a special working-up process. In this, after the reaction of the pyrrolizine with oxalyl chloride, the product obtained is treated with hydrazine and an alkali metal hydroxide in aqueous phase at elevated temperature; after treatment is complete a three-phase system is produced by addition of an ether which is not miscible or only limitedly miscible with water und ML 3000 is recovered by acidification of the middle phase. A polymorphic ML 3000 is obtained in high yield and pure, defined crystalline form.

As a whole, the synthesis takes place over the stages indicated in the following reaction scheme:

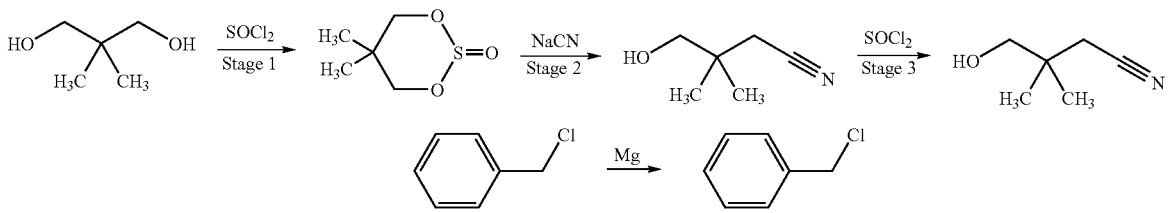

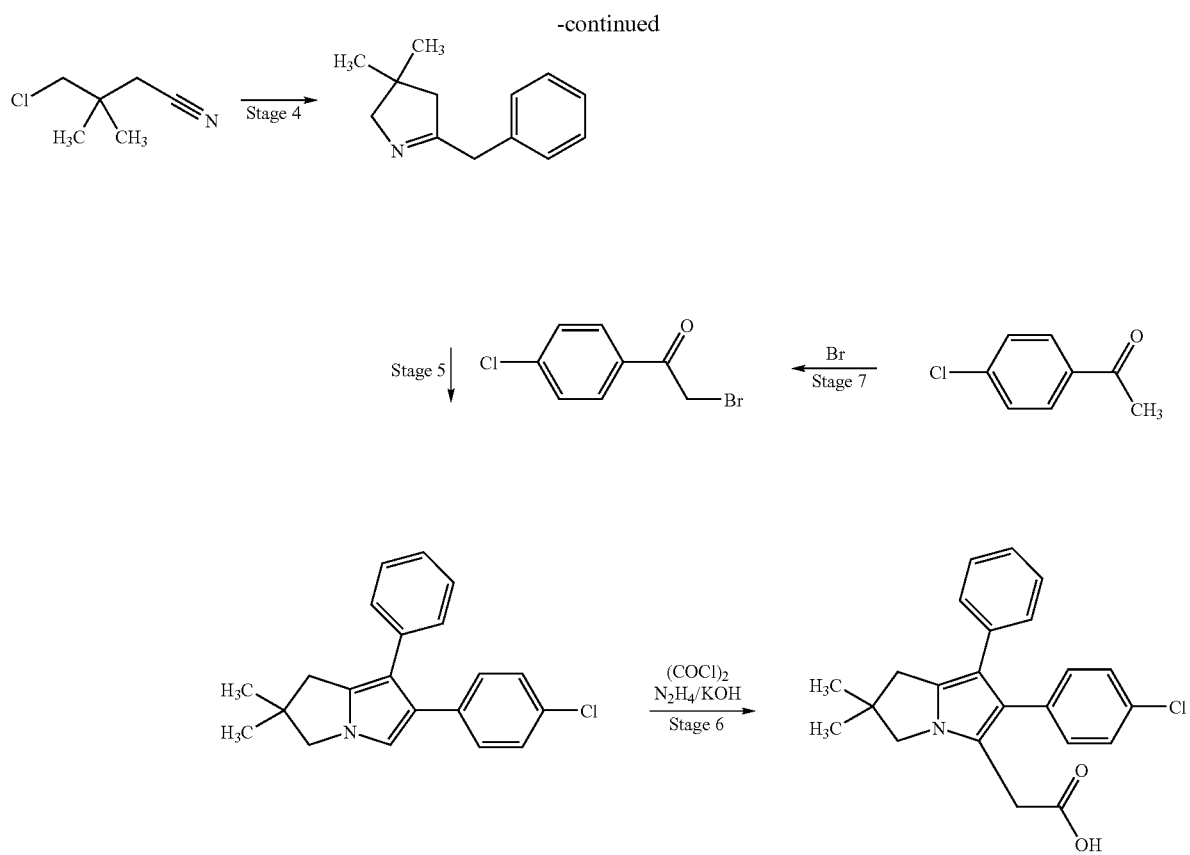

Stages 1 and 2 are known from EP 0 172 371 A1. The reaction of 2,2-dimethyl-1,3-propanediol with thionyl chloride is carried out in an inert organic solvent, e.g. a halogenated hydrocarbon or an ether, at preferably 0 to 60° C. The further reaction of the resulting 5,5-dimethyl-1,3,2-dioxathiane 2-oxide with sodium cyanide to give 4-hydroxy-3,3-dimethylbutyronitrile is carried out in DMSO at approximately 80 to 120° C. Stage 1 produces yields of approximately 93 to 99% and stage 2 produces yields of approximately 55 to 60% in good quality.

For stage 3, the reaction with thionyl chloride to give 4-chloro-3,3-dimethylbutyronitrile, a precursor of high purity is necessary. The crude products from stages 1 and 2 must be distilled before further reaction.

The 4-chloro-3,3-dimethylbutyronitrile obtained in stage 3 must also be distilled because of the high purity necessary for the subsequent Grignard reaction. With a required purity of 97%, the yields in stage 3 are unsatisfactory.

Additional technical problems result from the fact that the crude products from stages 1 and 3 originate from the reaction strongly acidic, which leads to the appearance of corrosion on the apparatus.

If the 4-chloro-3,3-dimethylbutyronitrile has the necessary purity, the addition of the benzylmagnesium chloride Grignard reagent in stage 4 to the 5-benzyl-3,3-dimethyl-3,4-dihydro-2H-pyrrole and the subsequent cyclization with ω-bromo-4-chloroacetophenone in stage 5 afford 6-(4-chlorophenyl)-2,2-dimethyl-7-phenyl-2,3-dihydro-1H-pyrrolizine in good quality and with a yield of 40 to 45% over both stages.

The pyrrolizine obtained in stage 5 is finally converted to 6-(4-chlorophenyl)-2,2-dimethyl-7-phenyl-2,3-dihydro-1H-pyrrolizin-5-ylacetic acid (ML 3000) by reaction with oxalyl chloride, followed by reduction using hydrazine in the presence of an alkali metal hydroxide and acidification. The yield in this stage 6 is, depending on purification of the product, about 62 to 86%.

The known process affords ML 3000 of acceptable purity and yield, but has some disadvantages, such as the problematic chemistry of the second and third stages, the need for laborious purification of the intermediates before further reaction, in particular before the Grignard reaction, long standing times, and corrosion problems on the apparatus during the purification of the strongly acidic reaction discharges from stages 1 and 3.

It is therefore an object of the present invention to make available a process for the preparation of 6-(4-chlorophenyl)-2,2-dimethyl-7-phenyl-2,3-dihydro-1H-pyrrolizin-5-yl acetic acid (ML3000) in which these disadvantages of the prior art are avoided. Using the process according to the invention, the overcoming of the technical difficulties in stages 1 to 4 of the previous synthesis, the avoidance of the awkward chemistry of the second and third reaction stages of the synthesis, the circumvention of the Grignard reaction, the raising of the overall yields, the lowering of the standing times and thus as a whole a more economical overall synthesis is desired.

The object is achieved by the process for the preparation of the compound of the formula I,

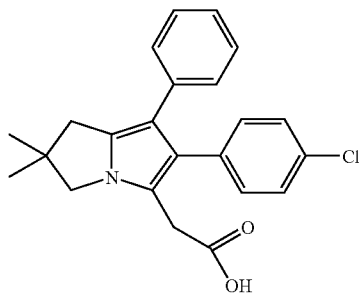

where
a) the compound of the formula IV

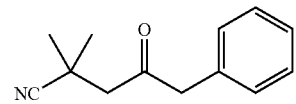

is converted into the compound of the formula III

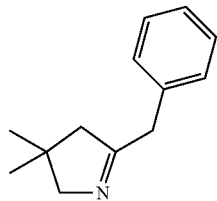

by
a1) catalytically hydrogenating the compound of the formula IV or
a2) converting the compound of the formula IV into the ketal of the formula IVa

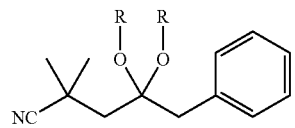

in which the radicals R, which can be identical or different, are $C_1$–$C_4$-alkyl or together are $C_2$–$C_3$-alkylene, and catalytically hydrogenating the ketal, b) reacting the compound of the formula III mit ω-bromo-4-chloroacetophenone to give a compound of the formula II

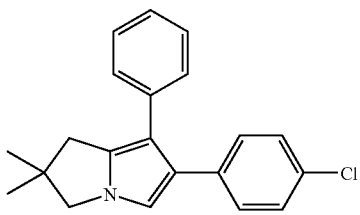

and c) introducing an acetic acid radical into the compound of the formula II.

The present invention also relates to a process for the preparation of the compound of the formula III by hydrogenation of a compound of the formula IV and ring closure, and to the corresponding process for the preparation of the intermediate of the formula II.

The introduction of the acetic acid radical into the compound of the formula II is preferably carried out by reaction with oxalyl chloride and reduction of the keto group, preferably using hydrazine and an alkali metal hydroxide.

The preferred process according to the invention can be illustrated by the following reaction scheme:

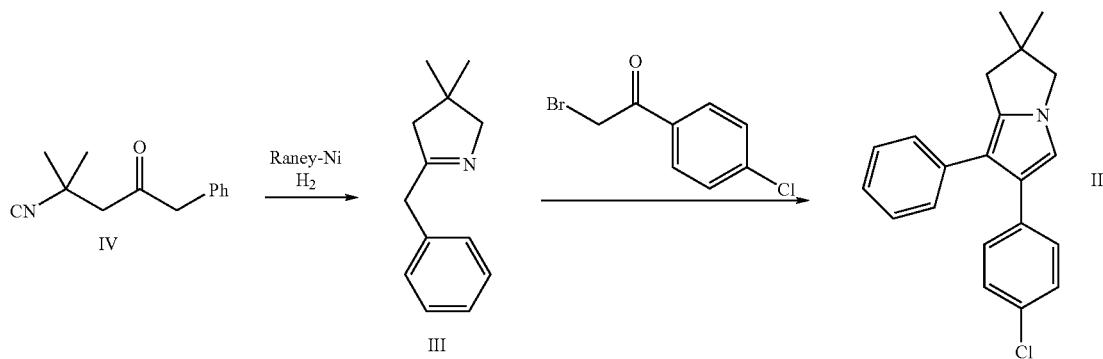

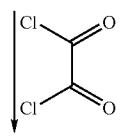

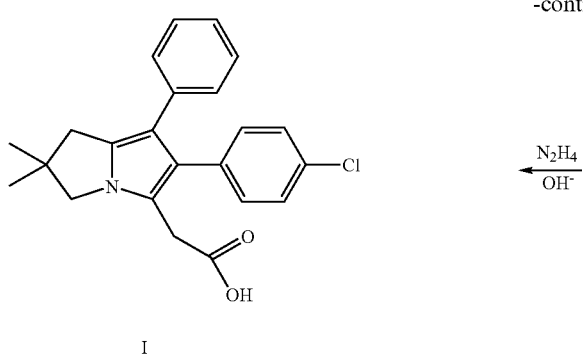

I

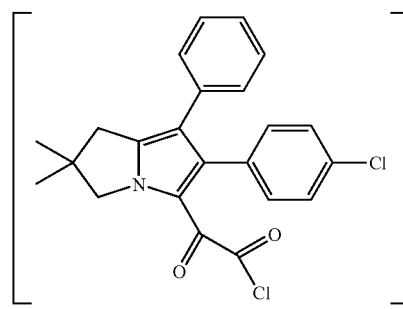

The synthesis of the compound IV is carried out according to the invention preferably via the following stages:

1. Preparation of 2-(N-methylanilino)acrylonitrile (V) from chloroacetaldehyde, N-methylaniline and an alkali metal cyanide, e.g. potassium cyanide.

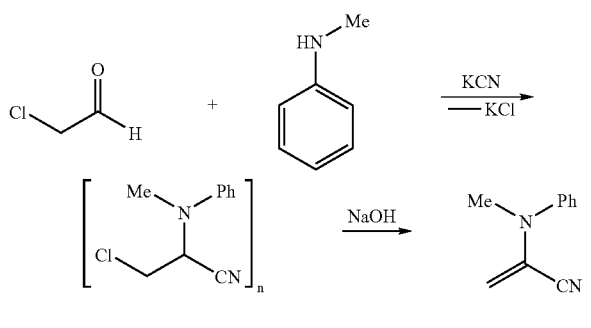

2. Preparation of 2,2-dimethyl-4-oxo-5-phenylvaleronitrile (IV) by Michael addition of isobutyronitrile, which has been deprotonated using a strong base, to the compound of the formula V, benzylation of the Michael addition product and hydrolysis of the resulting 2-benzyl-4,4-dimethyl-2-(N-methylanilino)glutaronitrile.

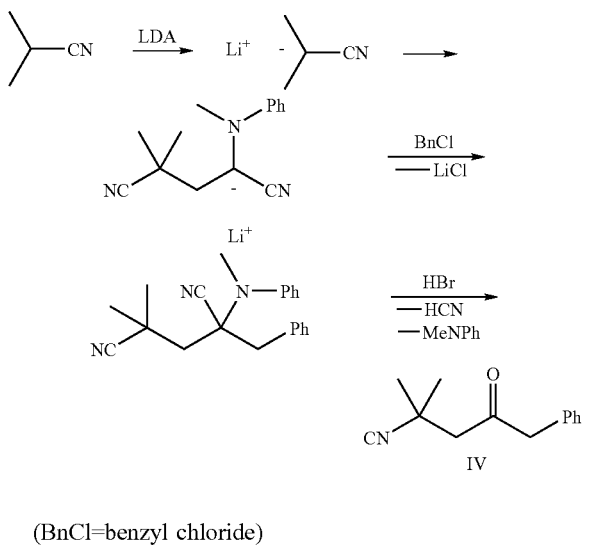

(BnCl=benzyl chloride)

The compounds of the formulae IV and V and their preparation are known. Thus, 2-(N-methylanilino)acrylonitrile (V) is prepared according to H. Ahlbrecht and K. Pfaff, *Synthesis*, 1980, 413. 2,2-Dimethyl-4-oxo-5-phenylvaleronitrile (IV) can be prepared according to H. Ahlbrecht and M. Ibe, *Synthesis* 1985, 421.

The process for the preparation of 2-(N-methylanilino) acrylonitrile (V) according to the literature procedure mentioned has the disadvantages, however, that a complete conversion does not take place either in the reaction with sodium or potassium cyanide or in the basic elimination, that ether is used for extraction and the product has to be distilled for purification, heavy losses occurring due to decomposition. According to the invention, it is therefore preferred to modify and to improve the literature processes and to combine them to give a multistage synthesis for the preparation of the compound of the formula III or of the formula II or I.

The improvements according to the invention are explained below. They can be used individually or, preferably, as a combination. According to the invention, the disadvantages mentioned are avoided in that the starting materials are employed in different molar ratios and/or N-methylaniline is introduced instead of chloroacetaldehyde and the reaction components are metered in and/or the elimination is carried out in a two-phase system hydrocarbon/sodium hydroxide solution with addition of a phase-transfer catalyst, preferably benzyltriethylammonium chloride. Preferred process conditions are indicated below:

Chloroacetaldehyde, N-methylaniline and potassium cyanide are employed in a molar ratio of 1.1 to 1.3:1:1.1 to 1.3, in particular approximately 1.2: 1:1.2. The addition of N-methylaniline proceeds exothermically, and cooling and/or rate of addition should be chosen such that the temperature does not exceed 25° C. For this purpose, N-methylaniline can be added, for example, to a mixture of ice and concentrated hydrochloric acid.

Chloroacetaldehyde is added, preferably as an aqueous solution, to N-methylaniline hydrochloride, a temperature of at most 20° C. being maintained by a suitable rate of addition and, if necessary, cooling. Potassium cyanide is then metererd in as an aqueous solution. By means of a suitable rate of addition and optionally cooling, an upper temperature limit of 20° C. is also maintained here.

The addition of N-methylaniline, chloroacetaldehyde and potassium cyanide can also be carried out at significantly lower temperatures, for example below 0° C. Temperatures near the upper limits mentioned are preferred, however, since they allow a more rapid addition and require a smaller outlay on cooling, without having a negative influence on yield and quality of the product.

If the N-methylaniline content of the suspension formed is below approximately 10%, a water-immiscible solvent, preferably an aliphatic or aromatic hydrocarbon, in particular toluene, is added and the intermediate 3-chloro-2-(N-methylanilino)propionitrile is extracted into the organic phase. The elimination is then carried out in the two-phase system toluene/sodium hydroxide solution. For acceleration and in order to achieve a complete elimination, a phase-transfer catalyst is added, preferably benzyltriethylammonium chloride. The temperature during the NaOH addition should not exceed 15° C.; after addition is complete it can rise to room temperature. The use of potassium hydroxide instead of sodium hydroxide in the elimination makes the phase separation difficult.

When the reaction mixture has reached a content of below 0.5% of 3-chloro-2-(N-methylanilino)propionitrile, the product phase is separated off and optionally washed, for example first with water and then with citric acid/water. The organic phase is then dried, for example using magnesium sulfate, and optionally filtered, preferably through a pressure filter. The solution of 2-(N-methylanilino)acrylonitrile in toluene thus obtained can be stored under nitrogen at −15° C. to −20° C. without problems until further processing. Decomposition does not take place at these temperatures. The product is obtained in an excellent yield of about 95%, based on methylaniline.

The cyanide-containing waste water and washing liquids and the filter residue are fed to a waste water treatment.

The process for the preparation of 2,2-dimethyl-5-phenyl-4-oxovaleronitrile (IV) by the literature procedure mentioned works up to the benzylation of the Michael addition product at −78° C. The benzylation is carried out using expensive benzyl bromide, and the hydrolysis and cyanide cleavage are carried out in acetonitrile and require a reaction time of approximately 40 to 50 hours. The crude product must be distilled.

In the modification according to the invention of the process for the preparation of the compound IV, a distillation of the crude product can be dispensed with. The purification is carried out exclusively by recrystallization. The cyanide cleavage is carried out in an aqueous/organic system with addition of a phase-transfer catalyst, whereby the reaction time can be considerably reduced. Moreover, the process according to the invention is uncomplicated in so far as it is not necessary to carry out the deprotonation and condensation at −78° C. Further, activation by means of carcinogenic hexamethylphosphoramide (HMPT) and the use of tetrahydrofuran, which is expensive and complicated to dry, are not necessary. Finally, the less expensive benzyl chloride can be used instead of benzyl bromide. Preferred process conditions are indicated below:

Isobutyronitrile is metered into a solution of a strong base in an inert solvent. A suitable strong base is, for example, sodium amide, sodium naphthalenide and preferably lithium diisopropylamide (LDA). The deprotonation is preferably carried out in a hydrocarbon, such as ethylbenzene, as solvent and at temperatures below 10° C. The compound of the formula V, preferably as a solution in toluene, is then metered in, the temperature likewise preferably being kept below 10° C. The rates of addition of isobutyronitrile and compound V are to be chosen correspondingly.

The preferred reaction temperature during the Michael addition is approximately −10 to −20° C.

When the content of compound V in the reaction mixture has fallen to below approximately 2%, benzyl chloride is metered in. Preferably, the addition is begun at low temperature (approximately −10 to −20° C.), and the mixture is later warmed, for example up to approximately 50 to 55° C.

When the content of 2,2-dimethyl-4-(N-methylanilino) glutaronitrile has fallen to below approximately 2%, which takes several hours, the cyanide cleavage is carried out. For this, the benzylated Michael addition product is in general not isolated, but it is converted into 2,2-dimethyl-4-oxo-5-phenylvaleronitrile (IV) by acidic hydrolysis with release of hydrogen cyanide and methylaniline with reformation of the carbonyl group. The hydrolysis is carried out after addition of water, preferably under phase-transfer catalysis. The phase-transfer catalyst used is preferably benzyltriethylammonium chloride or benzyldimethylhexadecylammonium chloride. The reaction temperature is in general in the range from approximately 20° C. to approximately 60° C. By the addition of the phase-transfer catalyst, the reaction time is reduced to approximately 15 to 18 hours. A further reduction in the reaction time can be achieved if up to approximately 20% by volume of methanol is added to the toluene phase and/or concentrated acid is used. For example, reaction times of only one hour at approximately 40° C. are then possible.

For the cyanide cleavage/hydrolysis, a strong mineral acid, such as, for example, hydrobromic acid or hydrochloric acid, is added and the reaction mixture is allowed to react, preferably at elevated temperature, until the content of benzylated Michael addition product has fallen to approximately 0.5%. The organic phase is then worked up in a customary manner and the toluene is distilled off. The temperature during the distillation should not exceed 50° C. The residue from the distillation can then be purified by recrystallization or subjected to coevaporation with isopropanol one or more times before recrystallization in order to remove toluene residues.

The recrystallization can be carried out in isopropanol, but toluene and mixtures of isopropanol and toluene are also highly suitable. Preferably, the product is recrystallized from two parts of isopropanol/toluene in the ratio 9:1.

Because of the good solubility of the compound IV in isopropanol, it is necessary, for crystallization, to cool, preferably to temperatures from −15° C. to −20° C.

Under certain circumstances, the product obtained can still be contaminated with Michael addition product, even after the recrystallization. Impurities of this type are not troublesome, however, as they can be easily removed during the further reactions. On the whole, the recrystallization, however, has a very high purification effect, such that the product is obtained in very pure form.

As the next reaction stage, the 2,2-dimethyl-4-oxo-5-phenylvaleronitrile (IV) obtained is catalytically hydrogenated to give 2-benzyl-4,4-dimethyl-1-pyrroline (III). Catalysts which can be used are noble metal catalysts, such as Pt or Pd. However, Raney catalysts are preferred, in particular Raney Ni and Raney Co.

In Arch. Pharm. 299, 518 (1966), the preparation of 2-(4-hydroxyphenyl)-4,4-dihydro-3H-pyrrole by hydrogenation of 4-oxo-(4-hydroxyphenyl)butyronitrile using Raney nickel is described. The hydrogenation according to the invention takes place when it is carried out analogously to the literature process, i.e. using water-containing Raney nickel in alcohols, but only sluggishly, and at elevated pressure or elevated temperature a marked overhydrogenation is observed.

Attempts were therefore undertaken to shorten the reaction time and to reduce the formation of by-products, in particular by overhydrogenation to give pyrrolidine. It is seen here that neither increasing the hydrogen pressure nor increasing the reaction temperature significantly reduces the reaction time, but that under these more energetic conditions the proportions of by-products, especially of partial hydrogenation products, of oligomeric condensation products and of overhydrogenated pyrrolidine, increase.

Surprisingly, it has now been found that the quality (purity) of the starting compound of the formula IV employed has a strong influence both on the time course and on the by-product distribution of the hydrogenation. The purer the starting material, the smoother and more problem-free the reaction proceeds. Preferably, the compound IV is used in a purity of over 90%, in particular of over 95% (m/m).

In the hydrogenation of the nitrile ketone compound of the formula IV using the pyrroline of the formula III, a tertiary nitrile group is reduced in two hydrogenation sub-stages to the neopentylamine group, which condenses spontaneously with the ketone group with elimination of water to give the cyclic imino group. The cyclic imino group of the pyrroline can be further hydrogenated to give the secondary cyclic amino group in the pyrroline. In order to prevent this, Raney nickel is used as a catalyst, but not, as customary, in water-containing form, but essentially anhydrous. As solvents, toluene and in particular mixtures of toluene and $C_1$–$C_4$-alcohols, such as methanol, ethanol, isopropanol, e.g. toluene/methanol in the volume ratio 8:2 to 6:4, have proven the most suitable.

A further possibility of suppressing the overhydrogenation consists in the introduction of an acetal (ketal) protective group for the keto group of the nitrile ketone, the compound of the formula IVa

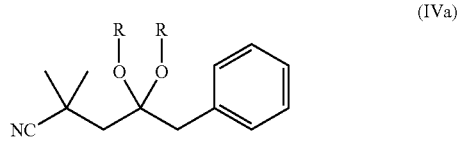

(IVa)

in which the radicals R, which can be identical or different, are a $C_1$–$C_4$-alkyl radical or together are a $C_2$–$C_3$-alkylene radical, being obtained. The hydrogenation of the tertiary nitrile group to the neopentylamine group can thus also be carried out under less selective conditions, a compound of the formula IVb

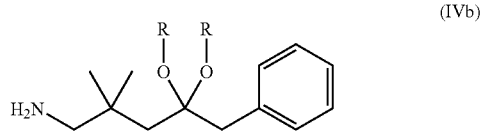

(IVb)

being obtained in which the radicals R have the meanings indicated. Under the conditions, the ketal cleavage takes place in acidic media, e.g. in dilute mineral acids, and simultaneously also the cyclization to the pyrroline. After alkalizing the acidic aqueous solutions of the pyrrolinium salts, the free pyrroline base is obtained, which is separated off using organic, water-immiscible solvents and, after removal of these solvents, can be obtained in highly pure form.

Preferred reaction conditions for the direct obtainment of the compound III by hydrogenation of the compound IV are indicated below:

If a mixture of toluene and methanol is used as a solvent, preferably approximately 8 to 12 parts by volume of toluene/methanol per part by weight of the compound V, the reaction temperature is in general approximately 50–60° C. If the hydrogenation is carried out in pure toluene, the temperature is chosen to be somewhat lower, for example 20–30° C., in order to prevent overhydrogenation. The hydrogen pressure is in general approximately 4 to 6 bar.

Before the reaction, the Raney nickel introduced is dried, for example by suspending one or more times with absolute methanol or by azeotropic distillation.

If the reaction comes to a halt before the absorption of the theoretical amount of hydrogen, the reaction mixture can be azeotropically distilled and fresh solvent can be added. Fresh Raney nickel can also be added and the mixture azeotropically distilled for the removal of water. The reaction in general lasts 3 to 4 hours.

The Raney nickel is then allowed to sediment and the supernatant reaction solution is filtered. The catalyst can optionally be used for further hydrogenations. The solvent is distilled off from the reaction solution. The product can be purified by salt formation, e.g. by hydrochloride formation and release of the compound of the formula IV using a base, for example ammonia, and re-extraction.

Alternatively, only a part of the solvent can also be distilled off, e.g. the methanol, in a solvent mixture of toluene/methanol. In this case, the distillation residue is advantageously first washed with water, and after separating off the water phase the product can be purified as described above.

In the reaction procedure according to the invention, the hydrogenation can in particular be strongly accelerated by using anhydrous Raney nickel as a catalyst and toluene or a mixture of toluene and methanol as a solvent and secondary reactions can be kept within limits.

The preferred reaction conditions for the obtainment of the compound of the formula III by means of the hydrogenation of cyclic or acyclic acetal (ketal) intermediates are indicated below:

The nitrile ketone of the formula IV is converted to the ketal in a solvent which forms an azeotrope with water, using an alcohol in the presence of an acid catalyst, or the conversion of the ketone to the ketal is carried out in an alcohol in the presence of equivalent amounts of an acetal or ketal of a low-boiling aldehyde or ketone. Suitable alcohols for ketal formation are $C_1$–$C_4$-alkanols, such as methanol, ethanol or glycol, 1,3-propylene glycol etc. Solvents which form an azeotrope with water are, for example, toluene, xylene, cyclohexane etc.

A preferred embodiment is, for example, the conversion to an oxolane derivative in toluene using ethylene glycol in the presence of an acid, such as toluenesulfonic acid, under reflux conditions and with removal of the water from the reaction mixture, e.g. using a water separator. A further preferred embodiment is the conversion to the dimethyl ketal in methanol using 1,1-dimethoxyethane in the presence of pyridinium tosylate at approximately 40 to 60° C. The ketals are then treated by washing with alkali and hydrogenated in the presence of a hydrogenation catalyst. A particularly preferred embodiment is the hydrogenation of the dioxolane derivative in the presence of anhydrous Raney nickel at a hydrogen pressure of 5 to 50 bar and at room temperature to 70° C. in alcoholic solvents, such as methanol, or in an aromatic solvent, such as toluene. The compound of the formula III is obtained after filtering off the catalyst by stirring the amino ketals obtained as a hydrogenation product from the organic phase into an aqueous dilute mineral acid. Both the cleavage of the ketals and the formation of the cyclic imine has taken place completely as a rule after 30 min to 1 h at RT. The cyclic imine III can be obtained in very pure form after alkalization of the aqueous product solution to pH 9 to 11.

The 2-benzyl-4,4-dimethyl-1-pyrroline of the formula III is then cyclized with ω-bromo-4-chloroacetophenone to give the 6-(4-chlorophenyl)-2,2-dimethyl-7-phenyl-2,3-dihydro-1H-pyrrolizine of the formula II. The reaction is known from the prior art mentioned at the outset. ω-Bromo-4-chloroacetophenone can be obtained, for example, as described in Bull. Soc. Chim. Fr. 21, 69 (1899).

The reaction of the compound of the formula III with co-bromo-4-chloroacetophenone is in general carried out in a polar organic solvent. Suitable polar organic solvents are in particular $C_1$–$C_4$-alcohols, such as methanol, ethanol, isopropanol or ethers, such as diethyl ether, tetrahydrofuran (THF), or dioxane. According to the present invention, methanol is particularly preferred as a solvent. The reaction components can be employed in equimolar amounts. However, it is preferred to use the ω-bromo-4-chloroacetophenone in an excess, for example in an excess of 10 to 40 mol %.

In order to trap the hydrogen bromide liberated in the reaction, it is carried out in the presence of a base. Preferably, an inorganic base, in particular an alkali metal hydrogencarbonate, or alkali metal carbonate, is used, the sodium and potassium compounds being particularly preferred. The inorganic base can be employed in the form of an aqueous solution. It has proven to be particularly preferred, however, to use the inorganic base in solid form. This facilitates the removal of the inorganic reaction products and reduces the by-product spectrum. The inorganic base can be employed in equimolar amounts, based on the amount of hydrogen bromide released. Expediently the inorganic base, however, is used in an excess, for example in an excess of up to 1.8 equivalents, preferably approximately 1.4 equivalents. Moreover, it is expedient to carry out the reaction with exclusion of light. The reaction temperature can be varied within a wide range and is preferably in a range from 0 to 50° C., particularly preferably approximately 18 to 25° C. The reaction is finished after approximately 17 to 20 hours.

The crude product of the formula II obtained is separated off, for example by centrifugation, and purified in a customary manner by removing the inorganic impurities. To this end, the crude product is preferably introduced into warm water, for example at 40 to 45° C., and treated for 1 to 2 hours. In this way, the compound of the formula II is obtained in a yield of on average 58% and with a purity of at least 97%. The content of the isomer containing the 4-chlorophenyl group in the 5-position is below 2%, the content of ω-bromo-4-chloroacetophenone is below 0.1% and the content of inorganic impurities is below 0.5%.

For the preparation of ML 3000 (I), an acetic acid side chain is introduced into the 5-position of the compound of the formula II. This is preferably carried out by reaction of the compound of the formula II with oxalyl chloride and subsequent reduction using hydrazine and an alkali metal hydroxide. The reaction is described, for example, in WO95/32971, example 5C, and in PCT/EP 01/00852. For the purification of the reaction product, different routes are described. According to WO95/32971, the reaction mixture is treated with water, acidified and the precipitated carboxylic acid is taken up in diethyl ether. The product is purified by stirring the ethereal solution over a drying agent, such as anhydrous sodium sulfate or magnesium sulfate, for some time and allowing it to stand, then filtering off the sulfate which is saturated with water and finally evaporating the ether in the presence of heat. The substance crystallizing from the mother liquor on concentration is collected and dried. In this process of isolation and purification, even in the purification step and during drying, some decomposition products are newly formed, so that a further laborious purification of the ML 3000, e.g. by recrystallization, is necessary in order to obtain pharmaceutical quality.

In the alternative purification process, after the reduction using hydrazine and an alkali metal hydroxide, an ether and water are added to the reaction mixture, optionally at relatively high temperature. Preferably, an ether which is limitedly miscible with water, e.g. diethyl ether or methyl t-butyl ether, is used. By means of the addition of the ether, a three-phase system is formed, the middle phase being the product phase, which essentially consists of the salt of ML 3000 with the alkali metal hydroxide used in the reaction. The uppermost phase is the ether phase in which the organic impurities are situated, and the lowermost phase is a strongly alkaline aqueous phase which contains the inorganic constituents.

The phases are separated and the middle phase is treated with a mixture of water and the ether which is only limitedly miscible with water, then acidified with an inorganic or organic acid. The ML 3000 is then dissolved in the ether phase.

The ML 3000 can be obtained from the ether phase, for example, by evaporation of the ether and crystallization of the ML 3000 from ethyl acetate or isopropanol. In this process, solvates containing 1 molecule of diethyl ether to 2 molecules of ML 3000 or containing 1 molecule of ethyl acetate to 2 molecules of ML 3000 are obtained.

An essentially solvent-free crystal modification of ML 3000 is obtained when a hydrocarbon boiling higher than the ether is added to the ether phase, the ether is optionally at least partially distilled off and the ML 3000 precipitated in solid, crystalline form is separated from the mother liquor in a customary manner. A hydrocarbon which can be used is in particular a straight-chain or branched aliphatic $C_6$–$C_2$-hydrocarbon, e.g. n-hexane, n-heptane, cyclohexane, cycloheptane, etc.

The following examples illustrate the invention without restricting it.

EXAMPLE 1

A) 2-(N-Methylanilino)acrylonitrile (About 50% Strength Solution in Toluene)

Conc. HCl (32%, 22.33 kg) and ice (32.6 kg) are introduced into a 250 l enamel reactor. N-Methylaniline (17.39 kg, 162.2 mol) is metered in with water cooling, without allowing the temperature to rise above 25° C. (30 min.). The green-yellow solution is stirred at 15–20° C. for 5–10 min. Beginning at this temperature, an aqueous solution of chloroacetaldehyde (45%, 34.2 kg, 196.1 mol) is metered in with water cooling such that the internal temperature is kept below 20° C. (30 min). The reaction mixture is stirred at 15–20° C. for a further 5–10 min beyond the mixing time and then treated at this temperature with a solution of potassium cyanide (12.7 kg, 195.1 mol) in water (19.5 kg). The addition is controlled here with water cooling such that a temperature of 20° C. is not exceeded (1 h). The mixture is stirred at a temperature of 18–23° C. for 110–130 min. A highly liquid suspension is formed. The gas-chromatographic sample indicates less than 10% methylaniline. Toluene (25.7 kg) and, subsequently with stirring, conc. hydrochloric acid (32%, 9.3 kg) are then added to the reaction mixture and it is stirred at RT for a further 5–10 min.

The hydrocyanic acid escaping from the apparatus is retained in an absorber filled with conc. NaOH.

With the stirrer switched off, the water phase (114 kg, cyanide waste water 1) is allowed to settle and it is transferred to a sealed system in a tank for disposal.

Benzyltriethylammonium chloride (0.3 kg) is added to the blue-colored organic phase and it is cooled to −5 to 0° C. When this internal temperature is reached, sodium hydroxide solution (30%, 32.6 kg) is allowed to flow in such that the internal temperature does not exceed 15° C. (30 min). After addition is complete, the reaction mixture is allowed to warm to RT and additionally stirred for a further 50–70 min.

The GC analysis of a sample shows a content of below 0.5% for the intermediate 3-chloro-2-(N-methylanilino)propionitrile. When this value is reached, the mixture is washed with water (40.7 kg): the water is added, the two-phase mixture is stirred for 5–10 min, then the water phase (79 kg, cyanide waste water 2) is allowed to settle and is transferred to the tank (to cyanide waste water 1).

The organic phase is washed again in the same manner with water (40.7 kg) which is acidified with citric acid (0.81 kg).

This citric acid/water phase (45 kg, cyanide waste water 3) is combined with the other cyanide waste waters. The organic phase is dried over magnesium sulfate (3.8 kg) at RT (room temperature) for 10–20 min. A Karl-Fischer titration shows a water content of below 0.2%. This toluene solution (50–52 kg) is filtered through a pressure filter and drawn off for use in the next stage. The filter residue (4.8 kg) is combined with the cyanide waste waters. These cyanide waste waters are fed to waste water treatment. The solution of 2-(N-methylanilino)acrylonitrile (53.86 kg), which is unstable at room temperature, is stored under nitrogen at −15 to −20° C. until further processing. For content determination, a 50 ml sample is drawn. A dry residue is determined from 30 ml of this sample by largely evaporating toluene in vacuo at a maximum of 70° C. For content determination, the integral areas of a 1 H-NMR spectrum of the sample in chloroform and a GC analysis are used. The content of 2-(N-methylanilino)acrylonitrile in the solution according to 1 H-NMR is 45.54%. The yield is thus 95.4% based on the methylaniline employed.

The treatment of the cyanide waste water is carried out using conc. $H_2O_2$ and NaOH 30% at pH 10–12 to a residual content of cyanide of below 30 mg/kg (<30 ppm).

B) 2,2-Dimethyl-4-oxo-5-phenylvaleronitrile

A lithium diisopropylamide solution in THF/n-hexane (LDA solution 25.1% w/w, about 2M, 80.7 kg, 188.7 mol) is poured into the dry apparatus (steel vessel, 250 l) flushed with protective gas and cooled to −15 to −20° C. under nitrogen by means of brine cooling. Isobutyronitrile (11.4 kg, 165 mol) is metered in with cooling such that the internal temperature does not exceed −10° C. After addition is complete, the vessel is rinsed (45 min) with toluene (2 kg).

The reaction mixture is stirred for 55–65 min at temperatures between −10 and −20° C. The toluene solution of 2-(N-methylanilino)acrylonitrile (47.1%, 52.8 kg, 157.2 mol) is then metered in with brine cooling at −20° C. such that the temperature in the interior does not exceed −10° C. (90 min). The supply vessel and the feedlines are rinsed with toluene (5.0 kg). The red-brown reaction mixture is stirred at −10 to −20° C. for 60–90 min. The content of starting material (2-(N-methylanilino)acrylonitrile) in a gas-chromatographic analysis is then below 2%.

With the cooling switched off, beginning at −10 to −20° C. benzyl chloride (23.9 kg, 188.8 mol) is metered in, allowing the internal temperature to rise to 5° C. On exceeding this temperature, the reaction is carried out with water cooling. When an internal temperature of 15° C. is reached, the mixture is warmed to an internal temperature of 50° C. at a heating rate of 20° C./h, while further benzyl chloride is metered in. The time required for the addition is 2.5 h.

The reaction mixture is kept at 50–55° C. for 3–4 h, and the content of 2,2-dimethyl-4-(N-methylanilino)glutaronitrile in a gas-chromatographic sample is then below 2%.

The batch is then cooled to below 25° C. and transferred to a vessel into which a threephase mixture of ice (22.6 kg), water (45.2 kg) and toluene (22.6 kg) is introduced (10 min). Toluene (14 kg) is used for rinsing. This toluene/water phase mixture is then warmed to 35–40° C., and the phases are allowed to separate. The clear bottom layer is removed (water phase, 75 kg) and the intermediate layer is left with the organic product phase.

Benzyltriethylammonium chloride (3.4 kg) and ice (34.7 kg) are first added to the organic phase and hydrobromic acid (48%, 69.4 kg, 411.6 mol) is then added at 0–15° C. in the course of 10 min. The temperature in the batch increases thereby to about 50° C. and hydrocyanic acid is driven off, which is retained in an absorber packed with sodium hydroxide solution (32%). After stirring at 50–60° C. for 6—6 h hours, a sample of the red-brown reaction mixture is withdrawn. The content of 4-benzyl-2,2-dimethyl-4-(N-methyl-anilino)glutaronitrile in the mixture should be below 0.5% according to GC analysis (GC=gas chromatography).

When this condition is fulfilled, the phases are allowed to settle at an internal temperature of below 60° C. for 10–15 min and the hydrogen cyanide-containing, HBr-acidic dark water phase (cyanide waste water 1, 90–110 kg) is transferred to a tightly sealed tank. The likewise dark-colored organic phase is cooled to below 30° C. and then extracted by stirring with a mixture of water (22.5 kg) and sodium hydroxide solution (30%, 2.5 kg) for 5–10 min at 15–25° C. The markedly paler-colored alkaline water phase (pH 10–14) is allowed to settle and is drained off into a tank for subsequent treatment (cyanide waste water 2.25 kg). The organic phase is then stirred with water (25 kg) at 15–25° C. for 10–15 min, and the water phase which is completely separated after 10–15 min is separated off to the alkaline cyanide waste water 2 (25 kg). The pH of this washing liquid should be 7–9.

The toluene phase is transferred to a distillation apparatus, and the vessel and supply connections are rinsed with toluene (5 kg). The toluene is distilled off completely in vacuo at a maximum of 50° C. (distillate 1a, 110–120 kg). The residue of the distillation is taken up in isopropanol (22.7 kg) and the solvent is then distilled off completely in vacuo up to a maximum internal temperature of 60° C. (distillate 1b, 23 kg). The azeotropic distillation with isopropanol (22.7 kg) is repeated again in the same manner (distillate 1c, 23 kg).

The residue of the azeotropic distillation is taken up at 25–30° C. with isopropanol (16 kg) and metered into a mixture of isopropanol (8.0 kg) and heptane (16 kg), to which crystal seeds of 2,2-dimethyl-4-oxo-5-phenylvaleronitrile (0.05 kg) are added for crystallization control. The supply vessel and connection lines are rinsed with isopropanol (2.0 kg). The crystal suspension is cooled to −15° C. to −20° C. and stirred for at least a further 2 h, but at the most 16 h. The crystal mass is filtered off with suction and resuspended in a precooled mixture of isopropanol (8 kg) and heptane (8 kg) at −15 to −20° C. for several min and filtered off with suction again. 26.7 kg of 2,2-dimethyl-4-oxo-5-phenylvaleronitrile are obtained as a moist crude material, in addition to a total of 66.9 kg of mother liquor. The crystals are dried in vacuo at 30–35° C., and after drying 22.3 kg (70.6%) of a product having a purity of greater than 90% remain after GC analysis.

C) Purification of 2,2-dimethyl-4-oxo-5-phenylvaleronitrile 2,2-Dimethyl-4-oxo-5-phenylvaleronitrile (85–90%, 22.3 kg, 110.8 mol) is suspended in a mixture of isopropanol (40.0 kg) and toluene (4.4 kg) in a 250 l enamel reactor and brought into solution completely by warming this mixture to 50–55° C. with stirring. The solution, which is then cooled to 25–30° C., is poured onto a stirred pressure filter filled with isopropanol (5 kg), and the solution is seeded with crystalline 2,2-dimethyl-4-oxo-5-phenylvaleronitrile (0.05 kg) and then slowly cooled to 5–10° C. It is stirred until a thick crystal suspension is formed. It is then cooled to −15 to −20° C. and stirred at this temperature for at least 2 h or overnight.

The product is filtered off on a suction filter and washed twice with isopropanol (4.8 kg each) precooled to −15 to −20° C. The moist crystal mass (26.6 kg) is dried at 30–35° C. in vacuo, and 16.6 kg of product (74.4% yield) having a purity of 96.1% (GC analysis) are obtained. The mother liquor (53.2 kg) is discarded.

D) 2-Benzyl-4,4-dimethyl-1-pyrroline

Raney nickel (7.7 kg), which has been freed beforehand of aqueous supernatant by decantation, is covered with a layer of nitrogen gas in a 250 l steel autoclave and then suspended in methanol (67 kg) for 15 min. After switching off the stirring, the Raney nickel is allowed to settle for 15–30 min and the methanol supernatant is forced off through a pressure filter covered with Dicalite® using nitrogen by means of a dip pipe. The catalyst is covered with a layer of the solution of 2,2-dimethyl-4-oxo-5-phenylvaleronitrile (13.2 kg) in toluene (92.4 kg) at 15–20° C. and treated with methanol (14.3 kg), which is used for rinsing the addition container of the toluene solution. The apparatus is filled three times with nitrogen to 3 bar and the pressure is released in order to displace atmospheric oxygen. It is then flushed three times with hydrogen at 1 bar and finally the hydrogen pressure is increased to 4.5–5.5 bar. The hydrogenation is started at 5.0 bar and 55–60° C. by switching on the stirring. The hydrogen absorption comes to a halt after about 3 h; in this time, 3.3 m³ of hydrogen are absorbed. The reaction mixture is cooled to 15–20° C., the stirring is switched off and the hydrogen overpressure is released. The apparatus is flushed 4 times with nitrogen and a sample is removed to check the reaction. The sum of unreacted starting material and overhydrogenated by-product should not exceed 10%. If the sample shows the required result, the reaction solution is subjected to clarifying filtration through a pressure filter covered with Dicalite® (0.5 kg). The apparatus and filter residue are rinsed with methanol (10 kg) and the methanol (kg) is then distilled off from the reaction solution at an internal temperature of 75–80° C. The residue of the distillation is cooled to 20–30° C. and washed with water (49.5 kg).

The two-phase mixture is stirred for 5–10 min, allowed to stand for 20–30 min for phase separation and the water phase (47–51 kg) is then removed. Ice (44 kg) and water (44 kg) and then concentrated hydrochloric acid (32%, 17.7 kg) are added to the organic phase at 15–20° C. and the mixture is stirred for 5–10 min. The HCl-acidic water phase has a pH of 1–2. The two phases are allowed to settle (10–20 min) and the aqueous pyrroline extraction phase is separated off. Marmite®, water, with which the waste line was rinsed, (5.6 kg) and toluene (86.9 kg) are added to this HCl-acidic aqueous product phase. Ammonia solution (24%, 17.7 kg) is added with cooling at a maximum of 25° C. The pH in the water phase of the phase mixture should be 9–11. The two-phase mixture is stirred for 5–10 min. The phases are then allowed to settle and the water phase is separated off. The toluene phase is transferred to a distillation apparatus with rinsing with toluene (5.5 kg) and the toluene is completely distilled off in vacuo at an internal temperature not exceeding 50° C. The toluene distillate obtained can be reused for extractions. The content of pyrroline is determined in an aliquot of the toluene phase (50 g), of which the dry residue is first determined by complete evaporation of the toluene in vacuo. This dry residue has a content of 70% of the sought 2-benzyl-4,4-dimethyl-1-pyrroline according to GC.

From 100.7 kg of product solution, with a dry weight content of 13.74% in the 50 g sample and a GC content of 74.1%, a yield of 54.7 mol of 2-benzyl-4,4-dimethyl-1-pyrroline is calculated. Based on oxovaleronitrile employed, a yield of 84% results.

E) 6-(4-Chlorophenyl)-2,2-dimethyl-7-phenyl-2,3-dihydro-1H-pyrrolizine

For the directly subsequent ring-closure synthesis of the pyrrolizine, ω-bromo-4-chloroacetophenone is employed in a 10 mol % excess (60.2 mol) and sodium hydrogencarbonate in a 36 mol % excess (74.4 mol) to the determined pyrroline (54.7 mol).

The distillation residue from stage D is treated at 15–20° C. with methanol (49 kg) then with sodium hydrogencarbonate (6.25 kg) and finally with cooling with ω-bromo-4-chloroacetophenone (14.06 kg). The resulting pale-yellow, highly liquid suspension is stirred with exclusion of light at 18–25° C. for 17–20 h. The suspension is centrifuged and the centrifugate is washed with methanol (11 kg) in two portions.

Methanol mother liquor and methanol wash solutions are disposed of. 16.5–18.5 kg of moist crude product are obtained, which is suspended in water (88 kg) and stirred for 1–2 h at 40–45° C. The crude product purified of inorganic impurities is centrifuged off and washed with water (22 kg) in 2 portions. The yield of moist crude product is 14–16 kg. The aqueous mother liquor and aqueous wash phases are discarded.

The crude product is dried at 35–40° C. in vacuo. On drying, the amount by weight reduces to 12.5–13.5 kg (38.4 mol –41.95 mol) of 6-(4-chlorophenyl)-2,2-dimethyl-7-phenyl-2,3-dihydro-1H-pyrrolizine of concentration 97.3% (HPLC). This corresponds to a yield of 71.0–76.7% based on the pyrroline obtained in the hydrogenation and a yield of 59–64% based on the oxovaleronitrile employed in the hydrogenation. The content of isomeric 5-(4-chlorophenyl)-2,2-dimethyl-7-phenyl-2,3-dihydro-1H-pyrrolizine is below 2%, the content of ω-bromo-4-chloroacetophenone below 0.1% and the content of inorganic impurities below 0.5% (ash determination).

EXAMPLE 2

Stages A) to D) were carried out as in Example 1.

E) 2-Benzyl-2-(2-cyano-2-methylpropyl)-1,3-dioxolane

Oxovaleronitrile (50 g, 0.25 mol) is treated with ethylene glycol (75 g, 1.21 mol) and p-toluenesulfonic acid (9.2 g, 0.048 mol) in toluene (300 ml, 260.1 g, 2.82 mol), and the reaction mixture is slowly heated to boiling (2.5 h). After a further 2 h reflux, the batch is checked by means of GC. The toluene is distilled off during the heating and reflux phase and replaced by dry solvent (185.3 g). The batch is placed in the cold under dry $N_2$ until work-up. For work-up, the toluene solution of the crude product is extracted with ice-cold sodium hydroxide solution (25 g, 0.625 mol NaOH on 150 g of ice) and the phases are separated. The organic phase is dried using anhydrous magnesium sulfate (MW 120.37, 50 g, 0.4 mol). After filtration, 245 g of filtrate are obtained.

F) 2-Benzyl-4,4-dimethyl-1-pyrroline

The crude solution of the dioxolane obtained under E) is introduced into a 1 l autoclave and 20 g of Raney nickel B113W (MW 58.71, 0.34 mol), which has been extracted three times beforehand with anhydrous methanol, together with 71.1 g of toluene are then added. By pressurizing with nitrogen three times and subsequent release, atmospheric oxygen is displaced from the autoclave. The hydrogenation starts after a hydrogenation pressure of 48 bar has been added using successive hydrogen additions and deaeration three times and the jacket temperature of the autoclave has been adjusted to 63° C. (time required 3 h). The hydrogenation in the 1 l autoclave requires refilling with hydrogen to the starting pressure value after about 3 h (internal pressure 23 bar) and after a further 18 h (internal pressure 17 bar). After a hydrogenation time of a total of 26.5 h, the mixture is allowed to cool and the reaction product is filtered through Decalite.

The cleavage of the acetal takes place directly following by taking up the crude product in dilute hydrochloric acid (HCl 32%, 50 g, 0.43 mol in $H_2O$, 200 g) and stirring at 30° C. for 1 h. The organic supernatant (toluene phase) is stripped off and the water phase is alkalized at 0 to 5° C. with aqueous concentrated ammonia (25%, 50 g, 0.73 mol) to a pH of 9 to 10. The precipitated pyrroline is taken up in diethyl ether (200 g) and separated off. After evaporation of the ether in vacuo, 32.1 g of product remain. The 2-benzyl-4,4-dimethyl-1-pyrroline is obtained in a yield of 69% and a purity of 92.6% (GC).

If the dioxolane is purified by distillation (92%, GC) before use in the hydrogenation, a higher hydrogenation rate at lower pressures (5 bar) and lower temperatures is achieved in the hydrogenation. The purity of the pyrroline obtained is 94–98% (GC).

EXAMPLE 3

Preparation of ML 3000:

A) 5-(4-Chlorophenyl)-2,2-dimethyl-7-phenyl-2,3-dihydro-1H-pyrrolizine 17.9 kg (95.5 mol) of 2-benzyl-4,4-dimethyl-1-pyrroline prepared according to Example 1 or 2 (based on content of pyrroline compound), 29.7 kg (127.2 mol, 1.33 equiv.) of o-bromo-4-chloroacetophenone and 226.6 kg of methanol are introduced into a reactor (500 l). After addition of 12.7 kg (151.2 mol, 1.58 equiv.) of sodium hydrogencarbonate, the mixture is stirred with exclusion of light at 17–24° C. with formation of a beige suspension. The reaction is continued until the residual content of pyrroline compound in the mixture is <5%. After 17 h, a sample is taken and tested for the content of pyrroline compound by means of gas chromatography. The analysis showed a content of 2%. The suspension is then centrifuged at an internal temperature of 18–22° C. and the solid obtained by centrifugation is washed with 14.4 kg of methanol in two portions. The still moist, slightly yellow product weighs 25.8 kg.

The still moist crude product (25.8 kg) is suspended in 150 kg of water, then warmed to an internal temperature of 50–60° C. in the course of 15 min and stirred at this temperature for 40 min. The suspension, which is cooled to 40° C. (40 min), is centrifuged and the pale-yellow, crystalline solid obtained by centrifugation is washed out with 27 kg of water in two portions. The product is dried in vacuo at 50–60° C. for 12–24 h. 18.6 kg of 6-(4-chlorophenyl)-2,2-dimethyl-7-phenyl-2,3-dihydro-1H-pyrrolizine are obtained, having a content of 0.33% of ash and an isomer content of 5-(4-chlorophenyl)-2,2-dimethyl-7-phenyl-2,3-dihydro-1H-pyrrolizine of 1.0%.

B) 6-(4-Chlorophenyl)-2,2-dimethyl-7-phenyl-2,3-dihydro-1H-pyrrolizin-5-ylacetic acid (ML-3000)

After evacuation three times and introduction of $N_2$, 11.5 kg (35.7 mol) of 6-(4-chloro-phenyl)-2,2-dimethyl-7-phenyl-2,3-dihydro-1H-pyrrolizine are introduced into 60 kg of tetrahydrofuran (THF) in a 250 l reactor. The yellow-colored solution is cooled to 10–15° C. under a 0.5 bar nitrogen supply ($N_2$). 6.8 kg (54.7) mol of oxalyl chloride are then metered in under $N_2$ from a supply vessel over the course of 35 min such that the internal temperature does not exceed 20° C.

After addition is complete, the now dark-green, thin suspension is stirred at an internal temperature of 18–25° C. for 20 to 30 min. 18 kg of ice in flakes are introduced into a 500 l reactor. The warm suspension at 25° C. is metered into this ice over the course of 5 min such that the internal temperature of the mixture does not exceed 20° C.

The reaction mixture is stirred at an internal temperature of 25–35° C. for 10–20 min. The still green solution is diluted with 62.2 kg of diethylene glycol at 25–35° C. 14.9 kg (298 mol) of hydrazine hydrate are then added from a supply vessel during the course of 10–15 min with cooling. The internal temperature rises to at most 40–45° C. By stepwise increase in the temperature during the course of 1.5 h, the now beige-colored suspension is warmed to an internal temperature of 70–75° C., THF distilling off. Until reaching an internal temperature of 75° C., 45.4 kg of THF distillate are collected.

The reaction mixture is cooled to 50–55° C. and treated in 8 to 10 portions divided over the course of 45 min with a total of 26.4 kg potassium hydroxide in flakes (KOH), the internal temperature rising to 65–70° C. even in the case of the first 5 kg of KOH and the initially thick suspension turning yellow, becoming highly liquid and gentle reflux occurring for a short time.

This suspension is now warmed to 90° C. at a temperature increase of 15° C./h, slight foaming commencing from 85° C. and the suspension thickening. At a temperature increase of 2° C./h, the internal temperature is now further raised to 102° C. and at the same time nitrogen is blown through the reaction mixture by means of the dip pipe at an increased speed of rotation of the stirrer. As a result of heavy foaming and additional evolution of gas, the volume of the reactor contents increases to double. If required, the reaction temperature is lowered by cooling. At an internal temperature of 100–105° C., the foam begins to collapse and a red-brown thin suspension results, which is now heated further to an internal temperature of 140–145° C. at a heating rate of 15° C./h. In the case of excessive foaming, the reaction temperature is lowered by cooling for a short time. At the same time, a number of aqueous distillates of a total of 44 kg are collected.

The batch is kept at 120–145° C. for 2–2.5 h. The reaction temperature is then cooled to 30–40° C. and 74.7 kg of water and 56.7 kg of diethyl ether are added. The reaction mixture is stirred at an internal temperature of 30–33° C. for 10–15 min, then the phases are allowed to settle. The resulting three-phase system is separated. The lowermost strongly alkaline aqueous phase, which weighs 154.9 kg, is colorless and only slightly turbid. It is disposed of as waste water. The yellow-colored, turbid intermediate phase of oily consistency weighs 29.6 kg and contains the main amount of product as the potassium salt. The uppermost, clear, yellow-colored ethereal phase is vigorously stirred into an extraction apparatus with 10 kg of water at an internal temperature of 30° C. for 10 min. The water phase is separated off 10 min after switching off the stirring. The intermediate phase (29.6 kg) and the aqueous extract of the ether phase (10.9 kg) are treated in an extraction apparatus with 126.2 kg of diethyl ether and 59.7 kg of water, and the mixture is cooled to an internal temperature of 0–5° C.

A mixture of 6.0 kg of 32.5% strength hydrochloric acid and 6.0 kg of water is now metered in via a supply vessel during the course of 15 min such that a maximum internal temperature of 10° C. is not exceeded and a pH of 1–2 is achieved. If this pH is not achieved, a further 0.2 kg of 32.5% strength hydrochloric acid as a mixture with 0.2 kg of water is added. After achieving this pH, the phases are thoroughly stirred for a further 5–10 min and then allowed to stand for 10–20 min for phase separation with the stirring switched off.

The HCl-acidic water phase is drained off. The ether phase is treated again via the supply vessel with a mixture of 9.5 kg of hydrochloric acid and 19 kg of water and thoroughly stirred at an internal temperature not exceeding 10° C. for 5–10 min. The phases are separated and the HCl treatment is repeated, if desired, up to 3 times.

The ether phase is then treated with 30 kg of demineralized water, thoroughly stirred during the course of 10–20 min and warmed to 15–20° C. The phases are separated and the extraction is repeated.

The ether phase washed free of traces of acid is treated with 6.5 kg of anhydrous magnesium sulfate and 0.4 kg of active carbon (Acticarbon 2S), which are suspended in 1 kg of diethyl ether, and stirred at 18° C. for 30–45 min. The suspension is subjected to clarifying filtration through a pressure filter covered with 0.5 kg of filtration aid (Cell flock) in a distillation apparatus. The filter and apparatus are rinsed with 8 kg of diethyl ether. 95.6 kg of heptane are added to the ether phase, and the ether is distilled off in vacuo at an internal temperature of 15–20° C. The crystal suspension resulting after distilling off the ether is cooled to an internal temperature of 13–18° C. and stirred at this temperature for 0.5–1.5 h. The crystals are then centrifuged off. The moist product obtained is washed with 23.0 kg of heptane in 2 portions. The moist product is dried at 50–60° C. overnight in a vacuum drying oven and, if desired, ground. 10.5 kg (77.2%) of ML-3000 having a melting point, determined according to the DSC method, of 157° C. are obtained. The IR spectrum corresponds to that of the reference standard.

What is claimed is:
1. A process for the preparation of the compound of the formula I,

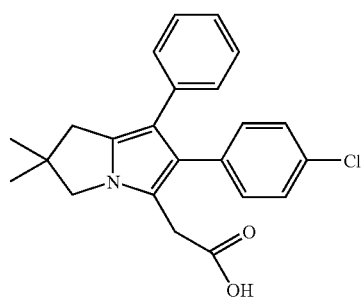

comprising converting
a) the compound of the formula IV

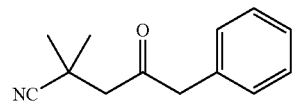

into the compound of the formula III

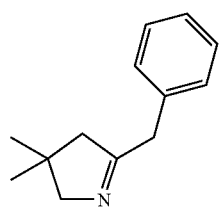

by
a1) catalytically hydrogenating the compound of the formula IV or
a2) converting the compound of the formula IV into the ketal of the formula IVa

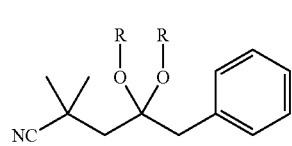

in which the radicals R, which can be identical or different, are $C_1$–$C_4$-alkyl or together are $C_2$–$C_3$-alkylene, and catalytically hydrogenating the ketal, b) reacting the compound of the formula III with ω-bromo-4-chloroacetophenone to give a compound of the formula II

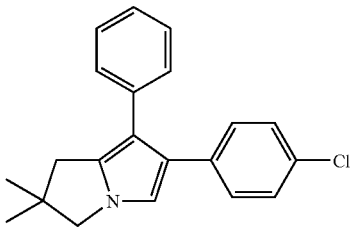
(II)

and c) introducing an acetic acid radical into the compound of the formula II.

2. A process for the preparation of the compound of the formula II

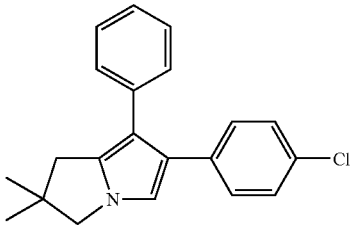
(II)

comprising converting the compound of the formula IV

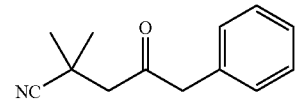
(IV)

into the compound of the formula III

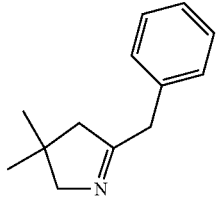
(III)

by a1) catalytically hydrogenating the compound of the formula TV or a2) converting the compound of the formula LV into the ketal of the formula IVa

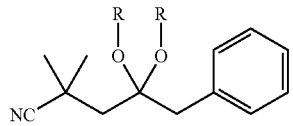
(IVa)

in which the radicals R, which can be identical or different, are $C_1$–$C_4$-alkyl or together are $C_2$–$C_3$-alkylene, and catalytically hydrogenating the ketal, and b) reacting the compound of the formula III with ω-bromo-4-chloroacetophenone to give a compound of the formula II.

3. A process for the preparation of the compound of the formula III

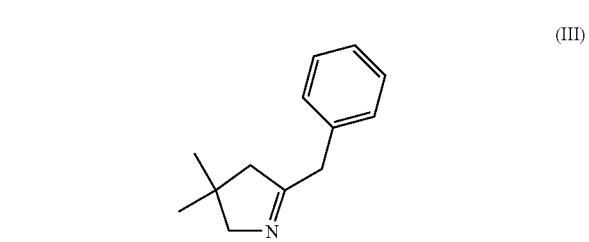
(III)

comprising converting the compound of the formula IV (IV)

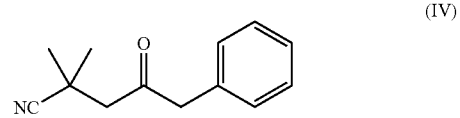

into the compound of the formula III by a1) catalytically hydrogenating the compound of the formula IV or a2) converting the compound of the formula IV into the ketal of the formula IVa

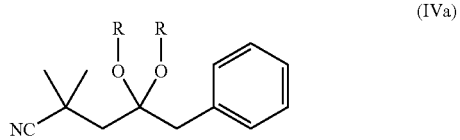
(IVa)

in which the radicals R, which can be identical or different, are $C_1$–$C_4$-alkyl or together are $C_2$–$C_3$-alkylene, and catalytically hydrogenating the ketal.

4. The process as claimed in claim 1, wherein anhydrous Raney nickel is used as a catalyst in the catalytic hydrogenation.

5. The process as claimed in claim 1, wherein the hydrogenation is carried out in toluene or a mixture of toluene and a $C_1$–$C_4$-alcohol as solvent.

6. The process as claimed in claim 1, wherein the compound of the formula IV is employed in a purity of at least 95%.

7. The process as claimed in claim 1, wherein the compound of the formula IV is obtained by Michael addition of isobutyronitrile to a compound of the formula V

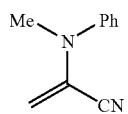

benzylation of the Michael addition product to give 2-benzyl-4,4-dimethyl-2-(N-methyl-anilino)glutaronitrile and hydrolysis of this nitrile.

8. The process as claimed in claim 7, wherein the isobutyronitrile is deprotonated using lithium diisopropylamide in toluene.

9. The process as claimed in claim 7, wherein the reaction temperature in the Michael addition is in the range of approximately −10° C. to −20° C.

10. The process as claimed in claim 7, wherein the hydrolysis of the nitrile in the acid is carried out in a two-phase system under phase-transfer catalysis.

11. The process as claimed in claim 7, wherein the compound of the formula V is obtained by reaction of chloroacetaldehyde, N-methylaniline and an alkali metal cyanide and subsequent basic elimination.

12. The process as claimed in the claim 11, wherein chloroacetaldehyde and then the alkali metal cyanide are added to N-methylaniline.

13. The process as claimed in claim 11, wherein the reaction is carried out in a molar ratio of approximately 1.1 to 1.3 parts chloroacetaldehyde, 1 part N-methyl-aniline and 1.1 to 1.3 parts alkali metal cyanide.

14. The process as claimed in claim 11, wherein the basic elimination is carried out in the two-phase system under phase-transfer catalysis.

15. The process as claimed in claim 2, wherein anhydrous Raney nickel is used as a catalyst in the catalytic hydrogenation.

16. The process as claimed in claim 2, wherein the hydrogenation is carried out in toluene or a mixture of toluene and a $C_1$–$C_4$-alcohol as solvent.

17. The process as claimed in claim 2, wherein the compound of the formula LV is employed in a purity of at least 95%.

18. The process as claimed in claim 2, wherein the compound of the formula IV is obtained by Michael addition of isobutyronitrile to a compound of the formula V

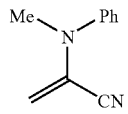

benzylation of the Michael addition product to give 2-benzyl-4,4-dimethyl-2-(N-methyl-anilino)glutaronitrile and hydrolysis of this nitrile.

19. The process as claimed in claim 18, wherein the isobutyronitrile is deprotonated using lithium diisopropylamide in toluene.

20. The process as claimed in claim 18, wherein the reaction temperature in the Michael addition is in the range of approximately −10° C. to −20° C.

21. The process as claimed in claim 18, wherein the hydrolysis of the nitrile in the acid is carried out in a two-phase system under phase-transfer catalysis.

22. The process as claimed in claim 18, wherein the compound of the formula V is obtained by reaction of chloroacetaldehyde, N-methylaniline and an alkali metal cyanide and subsequent basic elimination.

23. The process as claimed in the claim 22, wherein chloroacetaldehyde and then the alkali metal cyanide are added to N-methylaniline.

24. The process as claimed in claim 22, wherein the reaction is carried out in a molar ratio of approximately 1.1 to 1.3 parts chloroacetaldehyde, 1 part N-methyl-aniline and 1.1 to 1.3 parts alkali metal cyanide.

25. The process as claimed in claim 22, wherein the basic elimination is carried out in the two-phase system under phase-transfer catalysis.

26. The process as claimed in claim 3, wherein anhydrous Raney nickel is used as a catalyst in the catalytic hydrogenation.

27. The process as claimed in claim 3, wherein the hydrogenation is carried out in toluene or a mixture of toluene and a $C_1$–$C_4$-alcohol as solvent.

28. The process as claimed in claim 3, wherein the compound of the formula IV is employed in a purity of at least 95%.

29. The process as claimed in claim 3, wherein the compound of the formula IV is obtained by Michael addition of isobutyronitrile to a compound of the formula V

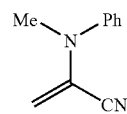

benzylation of the Michael addition product to give 2-benzyl-4,4-dimethyl-2-(N-methyl-anilino)glutaronitrile and hydrolysis of this nitrile.

30. The process as claimed in claim 29, wherein the isobutyronitrile is deprotonated using lithium diisopropylamide in toluene.

31. The process as claimed in claim 29, wherein the reaction temperature in the Michael addition is in the range of approximately −10° C. to −20° C.

32. The process as claimed in claim 29, wherein the hydrolysis of the nitrile in the acid is carried out in a two-phase system under phase-transfer catalysis.

33. The process as claimed in claim 29, wherein the compound of the formula V is obtained by reaction of chloroacetaldehyde, N-methylaniline and an alkali metal cyanide and subsequent basic elimination.

34. The process as claimed in the claim 33, wherein chloroacetaldehyde and then the alkali metal cyanide are added to N-methylaniline.

35. The process as claimed in claim 33, wherein the reaction is carried out in a molar ratio of approximately 1.1 to 1.3 parts chloroacetaldehyde, 1 part N-methyl-aniline and 1.1 to 1.3 parts alkali metal cyanide.

36. The process as claimed in claim 33, wherein the basic elimination is carried out in the two-phase system under phase-transfer catalysis.

37. The process as claimed in claim 1, wherein step a1) is carried out, the compound of the formula IV is used in a purity of 90%, and said catalytically hydrogenating is carried out with Raney nickel in toluene or a mixture of toluene and a $C_1$–$C_4$-alcohol.

38. The process as claimed in claim 1, wherein step a2) is carried out, and said catalytically hydrogenating the ketal is carried out with anhydrous Raney nickel at 5 to 50 bar in an alcoholic or aromatic solvent at a temperature in the range of from room temperature to 70° C.

39. The process as claimed in claim 37, wherein said Raney nickel is anhydrous Raney nickel.

40. The process as claimed in claim 2, wherein step a1) is carried out, the compound of the formula IV is used in a purity of 90%, and said catalytically hydrogenating is carried out with Raney nickel in toluene or a mixture of toluene and a $C_1$–$C_4$-alcohol.

41. The process as claimed in claim 2, wherein step a2) is carried out, and said catalytically hydrogenating the ketal is carried out with anhydrous Raney nickel at 5 to 50 bar in an alcoholic or aromatic solvent at a temperature in the range of from room temperature to 70° C.

42. The process as claimed in claim 40, wherein said Raney nickel is anhydrous Raney nickel.

43. The process as claimed in claim 3, wherein step a1) is carried out, the compound of the formula IV is used in a purity of 90%, and said catalytically hydrogenating is carried out with Raney nickel in toluene or a mixture of toluene and a $C_1$–$C_4$-alcohol.

44. The process as claimed in claim 3, wherein step a2) is carried out, and said catalytically hydrogenating the ketal is carried out with anhydrous Raney nickel at 5 to 50 bar in an alcoholic or aromatic solvent at a temperature in the range of from room temperature to 70° C.

45. The process as claimed in claim 43, wherein said Raney nickel is anhydrous Raney nickel.

46. The process as claimed in claim 1, wherein step a2) is carried out, followed by cleaving the ketal in an acidic medium.

47. The process as claimed in claim 2, wherein step a2) is carried out, followed by cleaving the ketal in an acidic medium.

48. The process as claimed in claim 3, wherein step a2) is carried out, followed by cleaving the ketal in an acidic medium.

* * * * *